(12) United States Patent
Zander et al.

(10) Patent No.: US 11,220,664 B2
(45) Date of Patent: Jan. 11, 2022

(54) MODULAR INCUBATOR SYSTEM

(71) Applicant: ERT Optik Dr. Thiel GmbH, Ludwigshafen (DE)

(72) Inventors: Robin Christopher Zander, Freudenberg (DE); Erwin Thiel, Siegen (DE); Stephan Irle, Siegen (DE)

(73) Assignee: S-Biosystems GmbH

(*) Notice: Subject to any disclaimer, the term of this patent is extended or adjusted under 35 U.S.C. 154(b) by 518 days.

(21) Appl. No.: 15/311,273

(22) PCT Filed: May 13, 2015

(86) PCT No.: PCT/EP2015/000984
§ 371 (c)(1),
(2) Date: Nov. 15, 2016

(87) PCT Pub. No.: WO2015/172882
PCT Pub. Date: Nov. 19, 2015

(65) Prior Publication Data
US 2017/0073628 A1    Mar. 16, 2017

(30) Foreign Application Priority Data

May 15, 2014  (DE) .................. 10 2014 106 877.7

(51) Int. Cl.
*C12M 1/00*    (2006.01)
*C12M 3/00*    (2006.01)
*C12M 1/34*    (2006.01)

(52) U.S. Cl.
CPC ............ *C12M 41/14* (2013.01); *C12M 23/44* (2013.01); *C12M 23/48* (2013.01); *C12M 23/52* (2013.01);
(Continued)

(58) Field of Classification Search
CPC ...... C12M 41/14; C12M 23/44; C12M 23/48; C12M 23/52; C12M 23/54; C12M 29/04;
(Continued)

(56) References Cited

U.S. PATENT DOCUMENTS 3,712,268 A * 1/1973 Reed .................. C12M 41/12
                                                            119/319
4,201,845 A    5/1980 Feder et al.
(Continued)

FOREIGN PATENT DOCUMENTS

CN          101283084 A      10/2008
CN          102191163 A       9/2011
(Continued)

*Primary Examiner* — William H. Beisner
*Assistant Examiner* — Danielle B Henkel
(74) *Attorney, Agent, or Firm* — Fish IP Law, LLP (57) ABSTRACT

An incubator (110, 140) for the reception of an individual sample carrier, a shelving system (100) for such incubators, a transport container for such incubators, as well as a modular system are suggested, wherein the incubators can be inserted and withdrawn (130) independently of one another, can be supplied with electricity, water and a gas via corresponding connections (150), and can communicate with a computer network via a wireless connection. Such a system reduces the risk of contamination or confusion in the lab and avoids interruptions in the monitoring and controlling of the environmental conditions in the respective incubators. These can rather independently maintain the most favourable environmental conditions for the respective samples, both during storage and also during a transport operation. The insertion and withdrawal of individual incubators from the shelving system does not, or only very briefly, interrupt the monitoring and control of the conditions in the interior of the incubators.

17 Claims, 5 Drawing Sheets

(52) U.S. Cl.
CPC ............ *C12M 23/54* (2013.01); *C12M 29/04* (2013.01); *C12M 29/20* (2013.01); *C12M 41/12* (2013.01); *C12M 41/34* (2013.01); *C12M 41/44* (2013.01)

(58) Field of Classification Search
CPC ...... C12M 29/20; C12M 41/12; C12M 41/34; C12M 41/44
See application file for complete search history.

(56) References Cited

U.S. PATENT DOCUMENTS

| | | | |
|---|---|---|---|
| 6,518,059 B1 | 2/2003 | Butts | |
| 2002/0006361 A1 | 1/2002 | Sanadi | |
| 2005/0158701 A1* | 7/2005 | West | C12M 41/48 435/3 |
| 2010/0316446 A1 | 12/2010 | Runyon | |
| 2011/0070631 A1 | 3/2011 | Kiyota | |
| 2011/0136225 A1* | 6/2011 | Vunjak-Novakovic | C12M 23/44 435/325 |
| 2014/0356849 A1* | 12/2014 | Wikswo | G01N 33/5005 435/1.2 |
| 2016/0319955 A1* | 11/2016 | Gebauer | B01D 29/90 |

FOREIGN PATENT DOCUMENTS

| | | |
|---|---|---|
| DE | 10 2005 036 763 A1 | 2/2007 |
| DE | 10 2006 044 091 A1 | 4/2008 |
| DE | 10 2010 012 790 A1 | 9/2011 |
| JP | 2006149232 A | 6/2006 |
| WO | 2007/014727 A2 | 2/2007 |
| WO | 2012/130865 A2 | 10/2011 |
| WO | 2012/098380 A1 | 7/2012 |

* cited by examiner

MODULAR INCUBATOR SYSTEM

FIELD OF THE INVENTION

The invention relates to an incubator, a shelving system, a transport container, as well as a modular incubator system. Such devices are primarily used in the microbiology field to grow, store, transport, etc., microbiological cultures or samples.

STATE OF THE ART

The use of a (large) standard incubator leads, in particular when multiple users are involved, to some serious disadvantages in the laboratory. Thus, there is a high risk of contamination between the individual samples because the sample carriers cannot be kept structurally separated from each other. Samples may only be kept when they accept substantially the same environmental conditions (temperature, humidity, air composition, etc.). If sample carriers having the same format are used (for example, microwell plates/microplates), there also exists a high likelihood of confusion among different samples. Moreover, the opening and closing of the incubator may lead to temperature variations, which cannot be fully compensated by the temperature control of the incubator. If samples have to be shipped, then a suitable transport system is required. For this, the samples must be transferred to the transport system, which involves a risk of contamination of both the samples and the environment, as well as further temperature changes.

Document U.S. Pat. No. 6,518,059 B1 discloses a small incubator, which is intended to receive a single microwell plate. Some of the disadvantages mentioned above may be solved by using such small incubators. In particular, the incubator disclosed in U.S. Pat. No. 6,518,059 B1 allows very high temperature stability of the sample to be achieved with a very small volume of the sample chamber and direct conductive heat transfer between the hot plate and the sample. A water reservoir in the sample chamber also serves for temperature stabilization, wherein water may be refilled from the outside without opening the sample chamber. It is intended that the temperature in the sample chambers of several incubators may be controlled via the temperature control unit of a so-called master incubator. This is disadvantageous because a special master incubator (or a separate control unit) is needed, and only samples with the same temperature requirements may be handled by this control unit. In addition, special adaptation and, in particular, control of the air composition is not possible in the case of these small incubators. Furthermore, space-saving storage of several of these incubators is only possible by freely stacking them above one another and side by side of one another, which causes a problem in particular when withdrawing individual incubators. This problem is further exacerbated in that each incubator must be wired separately.

Document DE 10 2005 036 763 A1 discloses a system of several small incubators (each receiving a respective sample carrier, for example, a microwell plate), which may be extended and reversed as simply as possible. To achieve this, the housings of the incubators are specifically designed to be stackable; furthermore, they have special connection elements only on their upper and lower sides to allow connection to incubators respectively above or below them. In addition, each of the incubators has its own temperature control unit with the associated control electronics, wherein the control electronics interact with a bus system. The bus systems of the incubators may be interconnected with each other via the connection elements, so that a central control unit connected to one of the incubators may individually control all the incubators of the system. Individual adjustment and control of the moisture and the air composition in the individual incubators is not possible in this incubator system, since it is not possible to feed water or water vapor and/or gas, if required, into the individual incubators via the dedicated connection elements without influencing the humidity or air composition in the other incubators. Another disadvantage is that the lower incubators cannot be withdrawn from a stack or replaced without dismantling the whole stack. In this case, the electrical coupling between the incubators has to be shut off, so that their temperature is not regulated during this period.

In addition, the use of the small incubators disclosed in U.S. Pat. No. 6,518,059 B1 or DE 10 2005 036 763 A1 is a problem when shipping the samples, as the temperature and other environmental conditions in the incubator cannot be regulated during transport. Furthermore, these systems are not suitable for transport, since the water that is optionally present in the reservoir, is open to the interior. This results in the water being distributed in the interior in an uncontrolled manner and possibly even pouring onto the sample upon movement of the system.

Currently no system is known that enables seamless transition from the stationary incubation of samples to the shipping of samples.

OBJECT

The object of the invention is to provide devices and an overall system which avoid the disadvantages of known incubator systems.

SOLUTION

This object is achieved by the inventions with the features of the independent claims. Advantageous developments of the inventions are characterized in the dependent claims. The wording of all claims is hereby incorporated by reference into this description.

An incubator to hold a single sample carrier is proposed. The individual sample carrier, for example a petri dish or a microwell plate ("microplate"), may thus be fixed in the interior of the incubator. Depending on the sample carrier provided, such an incubator may thus be designed in different sizes. Preferably, the size of the incubator will correspond to a predetermined grid.

The incubator has individual supply connections for electricity, at least one gas (e.g. air, $O_2$ or $CO_2$) and vaporous or liquid water. It has means for controlling valves to adjust the gas and water flow entering via the supply connections, wherein the gas content and humidity may be influenced. The valves do not need to be installed in the incubator. They may be located, for example, at the external counterparts to the supply connections of the incubator and are regulated, for example, via a data interface or the like.

Furthermore, the incubator has means for establishing a wireless link (e.g. radio or infrared) with at least one computer or computer network, wherein the means are configured to establish a wireless connection so that the actual and/or target values for the gas content and humidity may be queried and/or adjusted and/or regulated by controlling the valves when a wireless connection is established.

Such incubators enable the individual sample carriers to be stored structurally separate from each other, whereby contamination and confusion in the laboratory may be greatly reduced. Unnecessary temperature changes are avoided. In addition, the different samples in the different incubators can be exposed to very different environmental conditions (temperature, humidity, air composition, for example, the $CO_2$ content of the air), and these conditions can be set independently in the different incubators.

Data and control commands may, for example, be directly exchanged with a PC via the wireless link, or the data may, for example, be transmitted to a server. This server may be local or, for example, may be installed with an Internet Service Provider and allow specific access to current incubator data and data histories. Access to this data may be effected, for example, by using client software (for example, a web browser) that is platform independent (i.e. computers, etc. with different system architectures and/or operating systems).

In particular, closed continuously-monitored cell incubation is increasingly important due to the significant development of cell biological therapies. It is even mandatory in human medical applications. This cannot be provided by any system known from the prior art.

It is advantageous if the incubator has sensors to determine the temperature, the humidity and the content of the at least one gas in the interior of the incubator, and, in addition, comprises a temperature control unit. In this way, temperature, humidity and air composition may be monitored and documented, while the temperature of an incubator may be controlled independently of other incubators.

In an advantageous development, the incubator also has a built-in control unit, for example, a controller for automatically controlling the gas and water flow entering the supply connections, as well as the temperature. The electronics of each incubator may autonomously control the temperature, humidity and gas atmosphere based on predetermined parameters.

It is advantageous, furthermore, if the control unit is arranged in a detachable module. In this way, the construction of the incubator is modular, allowing easier repairs or improvements to be made to the control unit, for example, to adapt it to technical developments.

It is also advantageous if the incubator has storage for electrical energy. This is preferably in the form of a battery or an accumulator. This allows the incubator to be temporarily operated autonomously in the event of a power failure or no connection to the external power supply. Short distance transport is also possible in this way.

In order to avoid overpressure occurring in the incubator, it may have a gas outlet.

To avoid contamination of the supply connections and/or the ambient air as well as the interior of the incubator, a development of the incubator also comprises a correspondingly designed filter system for the supply connections and/or the gas outlet.

Moreover, it is advantageous if the incubator has a unique identification address. Preferably, this is an individual IP address.

In addition, the incubator may include a data logger, which temporarily stores the values currently determined by the sensors if there is no connection with at least one computer or computer network. Once a connection to a network (server) or a PC is made, the cached values may be transferred to it. This will ensure that the documentation of the conditions in the incubator is continuous even in the event of the wireless connection not being maintained without interruptions.

In one development of the invention, the incubator comprises a lower and an upper shell.

The temperature stability in the incubator may be improved by the lower and upper shell being made of thermally insulating material.

In the event of contamination of the inner area of the incubator, it is of particular advantage if the lower and the upper shell each comprise an inner shell and an outer shell. This allows the inner shell to be easily cleaned or completely replaced.

A further embodiment of the incubator may have means to establish a USB and/or Ethernet connection with at least a computer or computer network, in addition to the means to establish a wireless connection.

In order for the liquid medium in the sample carrier not to pour out of the sample carrier into the entire inner area of the incubator during transport, it is advantageous if the sample carrier is closed by means of a semi-permeable membrane. This film should be permeable to gases and impermeable to liquids. It is advantageous if the incubator has a suitable device to press the membrane onto the sample carrier.

The object is further achieved by a shelving system for the above-mentioned incubators, wherein the dimensions of the incubators correspond to a grid and may have identical or different sizes. This shelving system may accommodate a plurality of such incubators, while maintaining the pitch of the incubators. These dimensions, in turn, match the sample carrier type for which the respective incubators are provided. Incubators arranged below may thus be withdrawn from or inserted into the shelving system without affecting the incubators above. In addition, the shelving system has supply connections for electricity, at least one gas, and vaporous or liquid water for each of the plurality of individual incubators. Preferably, there are regulatable valves at the supply connections to adjust the gas and water flow, enabling the gas content and humidity in the incubators to be influenced.

It is advantageous if the shelving system comprises a data interface for each of the plurality of incubators. This allows, for example, valves at the supply connections to be regulated by the control units of the respective incubators.

A further development of the shelving system is a locking mechanism that is suitable for fixing individual incubators in the shelving system, and allowing them to be released again independently.

Furthermore, a transport container is proposed for the incubators described above, which is adapted to receive at least one such incubator. The transport container has a storage device for electrical energy, preferably a battery or an accumulator. This is connected to means that may provide the at least one incubator with electric current. In this case, the electrical energy storage device is so dimensioned that the number of incubators, which the transport container may receive, may be supplied for a predetermined transport duration.

The transport or shipping of samples may be effected with such a transport container without the samples having to be taken out of the incubators, and without the electricity supply to the incubators having to be interrupted for significant periods.

Preferably, the transport container comprises reservoirs for water and at least one gas, e.g. $CO_2$, which are connected to means that may provide the at least one incubator with at least one gas and vaporous or liquid water. In this case, the reservoirs are so dimensioned that the number of incubators which the transport container may receive, may be supplied for a predetermined transport duration.

The supply of incubators with gas and/or water is thus not interrupted for significant periods. Thus, a substantially seamless transition from the stationary incubating of samples to the shipping of samples is achieved.

It is advantageous if the part of the transport container, which may receive the at least one incubator, has thermal insulation.

Uninterrupted documentation of the conditions in the incubators during transport may be obtained, wherein the transport container is equipped with means for recording the values determined by the sensors of the at least one incubator, when the at least one incubator is located in the transport container.

The object is also achieved by a modular incubator system with a shelving system, a plurality of incubators and at least one transport container, as described above.

Such a system reduces contamination and confusion in the laboratory and avoids lengthy interruptions in the monitoring and control of environmental conditions in the various incubators. These may rather maintain favorable environmental conditions for the respective samples independently, both during storage and during transport. In addition, the adding and removal of individual incubators to/from the shelving system does not, or only very briefly, interrupt the monitoring and control of the conditions inside the incubator.

Further details and features will become apparent from the following description of preferred embodiments in conjunction with the dependent claims. The respective features may be used on their own or together in combination. The possibilities for achieving the object are not limited to the embodiments.

The embodiments are shown schematically in the figures. The same reference numerals in the individual figures denote corresponding elements that are identical or functionally identical.

Figure 1:
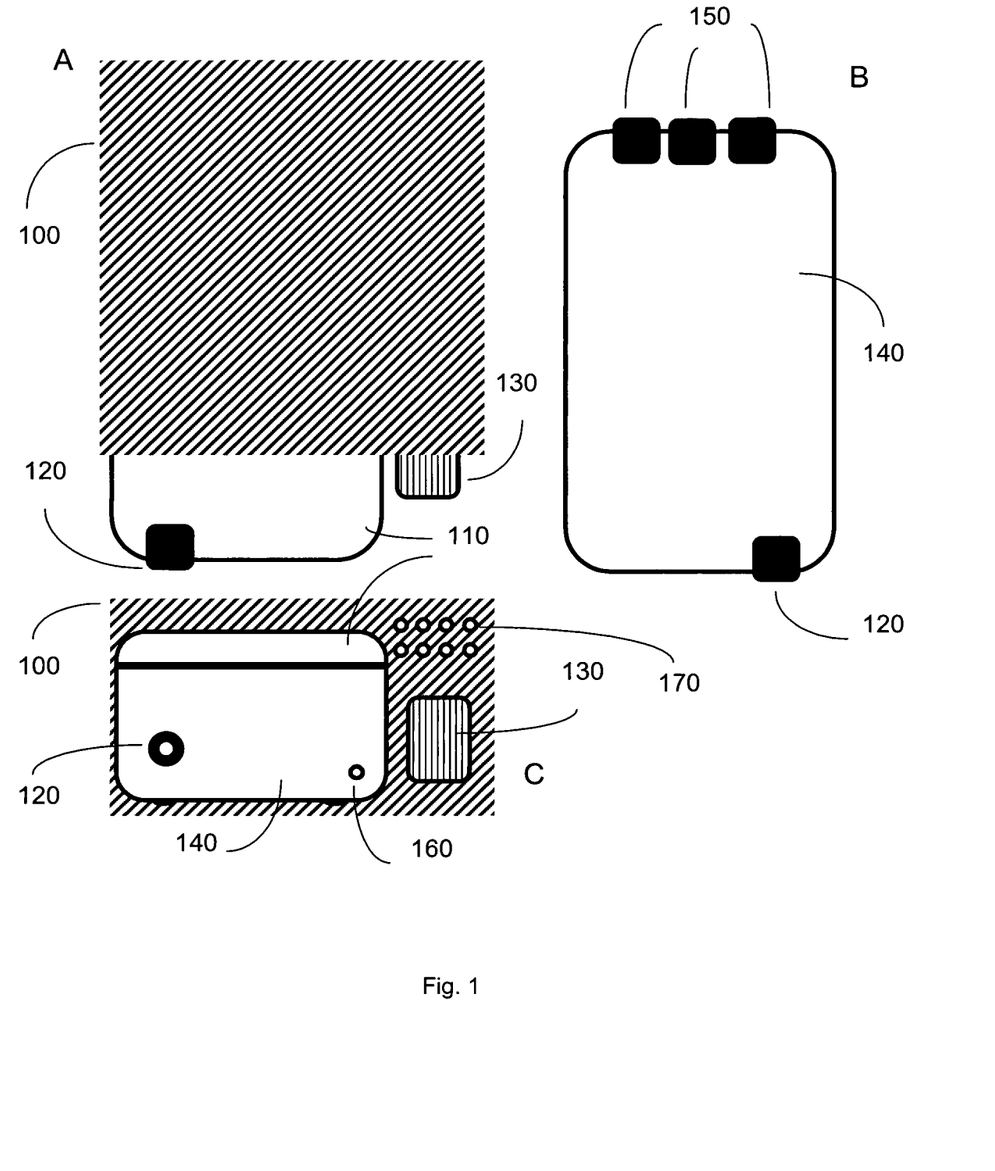
FIG. 1A shows a schematic plan view of an incubator according to the invention, which is located in a shelving system according to the invention.
FIG. 1B shows a schematic representation of the incubator from below (without the shelving system)
FIG. 1C shows a schematic front view of the incubator in a shelving system according to the invention.

FIG. 1 shows an incubator, which is dimensioned for a single sample carrier, typically a microwell plate.

FIG. 1A shows the incubator in a suitable shelving system (section) 100 in a plan view. One may see the top 110 of the incubator, the gas outlet 120 of the incubator as well as the locking switch 130 on the shelving system. By activating this switch, the lock is released, so that the incubator may be withdrawn from the shelving system. Appropriately, the supply of the incubator with electricity, water and $CO_2$ is interrupted by activating the switch 130.

FIG. 1B shows the underside 140 of the incubator. The connections 150 for electricity, water and $CO_2$ are located on the rear wall of the incubator. This allows them to be connected with the existing connections upon insertion into a compartment of the shelving system. Upon withdrawal of the incubator (after the lock has been released), these connections are separated again. There is a gas outlet 120 at the front of the incubator to prevent the creation of an overpressure in the interior of the incubator.

FIG. 1C shows this incubator from the front (in the associated shelving system 100). The incubator comprises two shells, an upper shell 110 and a lower shell 140. In addition to the gas outlet 120, there is a control lamp on the front side of the incubator 160 to indicate, for example, the proper supply to the incubator. The shelving system 100, in addition to the unlocking switch 130, comprises additional indicator lights 170 in order to indicate the details of the supply to the incubator, such as whether water and/or $CO_2$ is being introduced and/or whether the heater is in operation. In other embodiments, such control lights may be attached to the shelving system rather than to the incubator.

Figure 2:
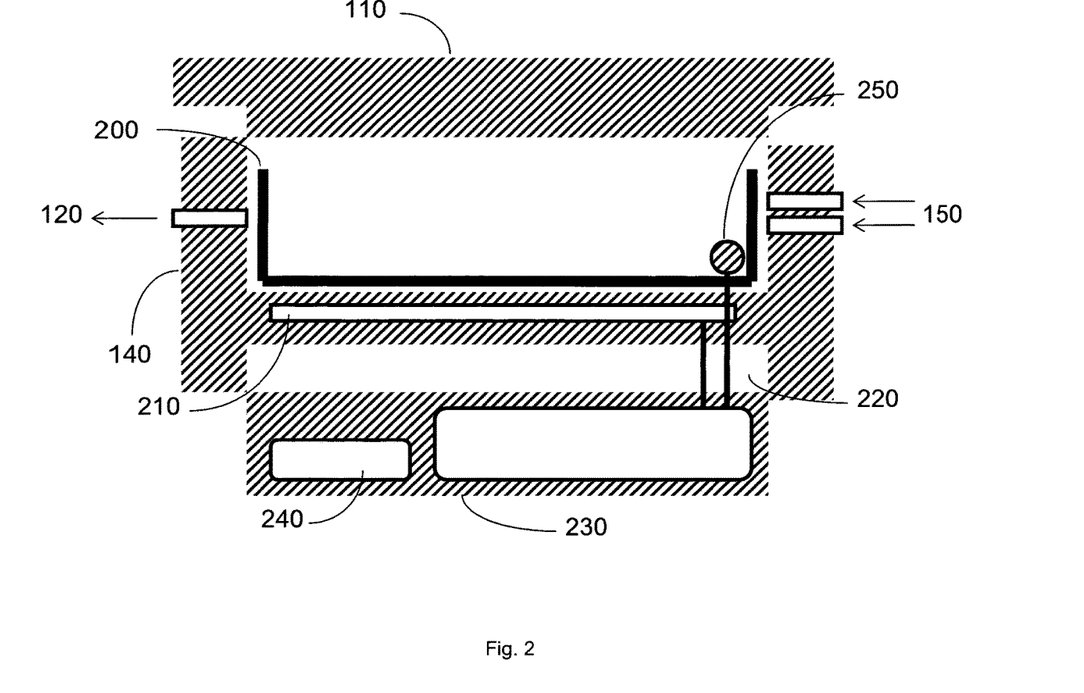
FIG. 2 shows a schematic longitudinal section in a side view through a modular incubator according to the invention.

The incubator shown in FIG. 2 as a longitudinal section in a side view, is of a modular design. The incubator essentially comprises an upper shell or a cover 110, as well as a lower shell 140 that surrounds an inner shell 200 in which the sample carrier may be kept. In the event of contamination of the incubator, this inner shell 200 may be easily replaced, so that the incubator may be used further without too elaborate measures having to be implemented. A heating element 210 is arranged underneath the inner shell 200. There are connections 150 at the rear end for $CO_2$ and water, while the gas outlet 120 is at the front end. There is a recess 220 in the lower area of the lower shell 140, in which the electronic module is 230 is inserted. This contains the control for the heating element and also for the regulation of the water and the $CO_2$ supply, as well as a data interface and a radio unit which allows the establishment of a wireless connection (WLAN) to a computer network. There is also a data logger located here. Furthermore, there is an accumulator 240 that allows fully autonomous operation of the incubator for a short period. Sensors 250 are located inside for temperature, humidity and air composition to allow effective control of the incubator, and which are connected upon insertion of the electronics module 230.

Figure 3:
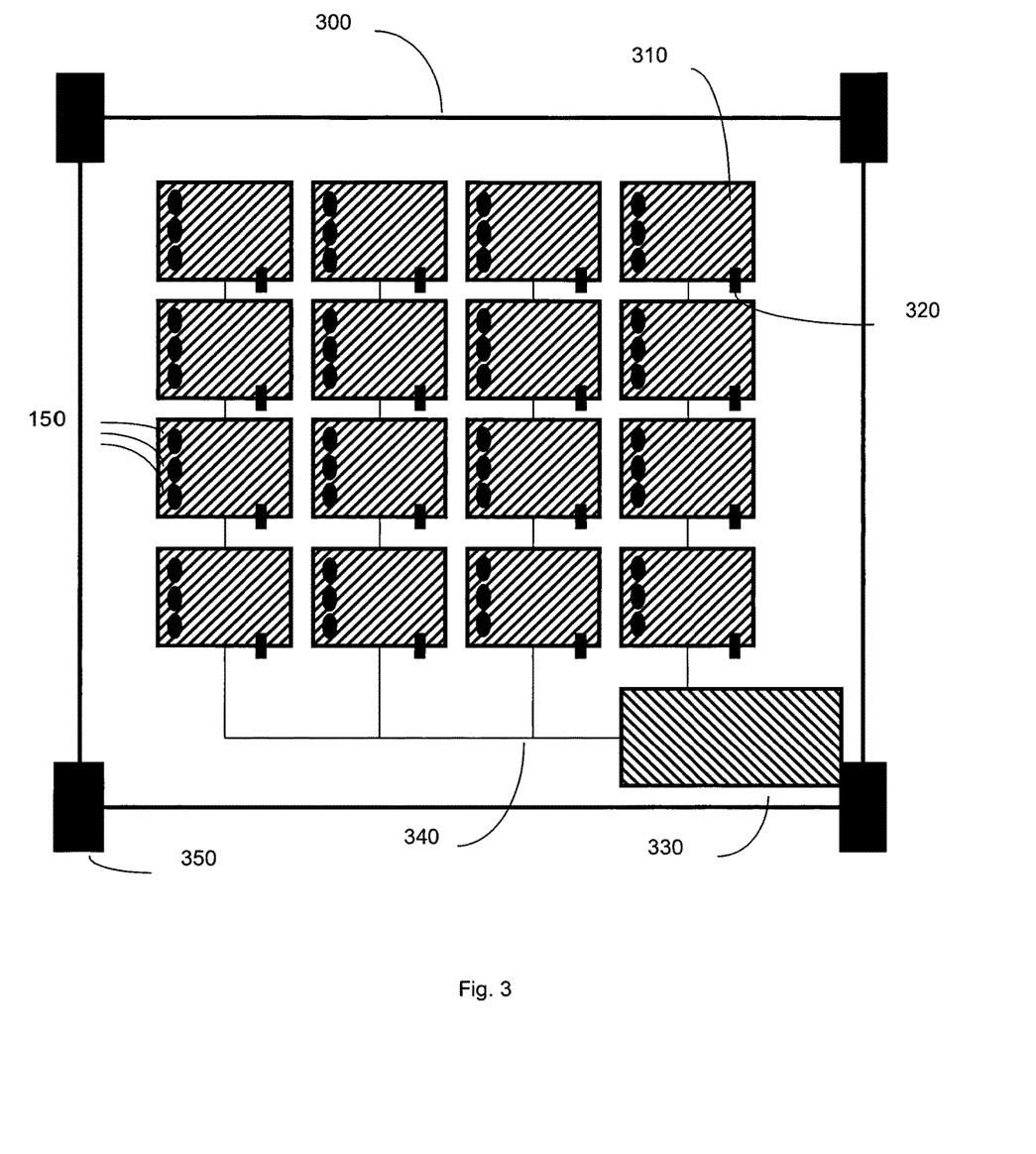
FIG. 3 shows a schematic representation of a shelving system according to the invention in a front view.

A shelving system 300 according to the invention is shown schematically in FIG. 3 in a front view. Its grid is so chosen that the shelving system may accommodate sixteen of the smallest provided incubators 310 (in 4 levels). These incubators 310 might, for example, each be sized to receive a petri dish as a sample carrier. Guiding and locking devices 320 ensure that the incubators 310 may be easily inserted in the shelving system 300 and removed again, while the incubators 310 may be fixedly connected to the shelving system 300, so that these may not be removed unintentionally. The shelving system 300 has a power supply unit 330 and leads 340 to the individual receiving points, whereby the incubators 310 may be supplied with electricity, water and $CO_2$ via corresponding connections 150 (arranged on the rear side in this embodiment). In addition, the features of this shelving system 300 include system assembly connectors 350 at the corners which allow several such shelving systems to be connected together, or even mounted on a wall or in a rack system.

Figure 4:
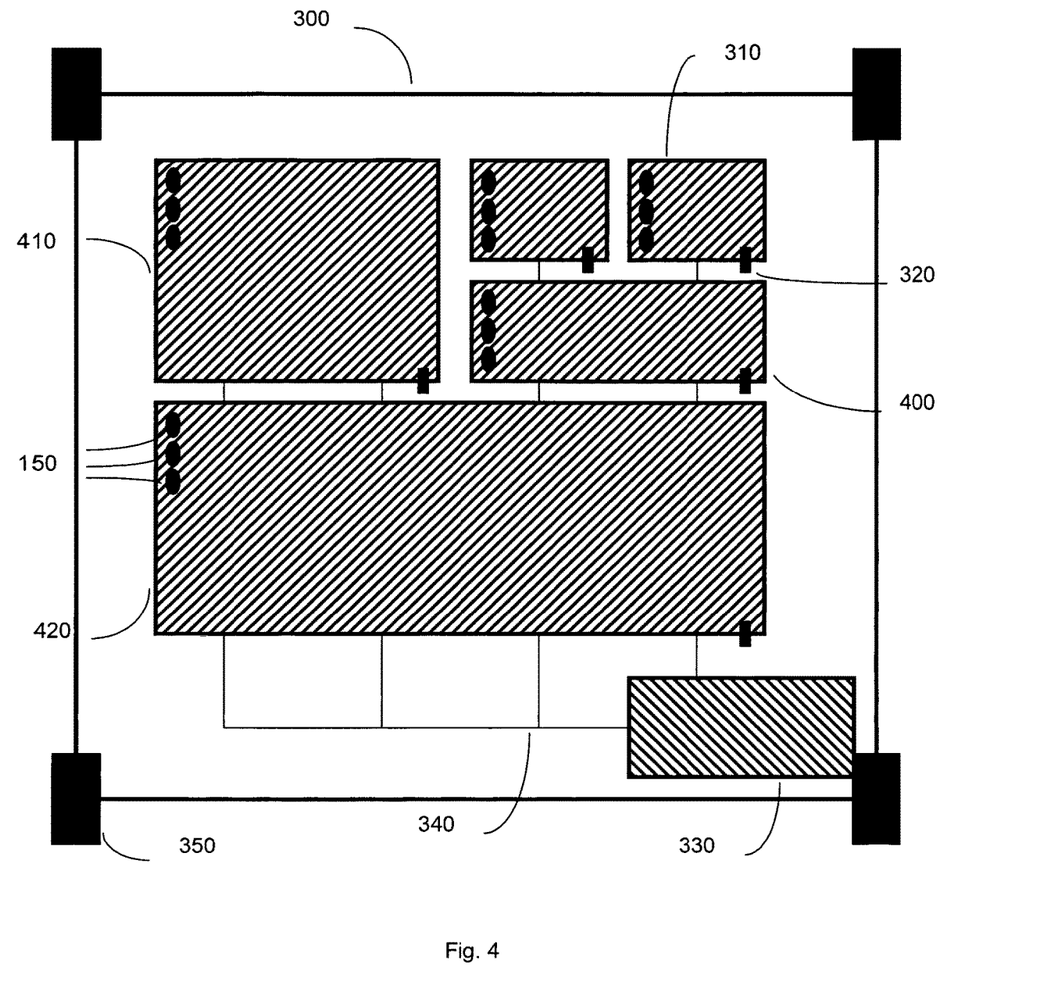
FIG. 4 shows a schematic representation of a shelving system according to the invention with different sized incubators according to the invention.

FIG. 4 shows the same shelving system 300 as shown in FIG. 3, with the difference that larger incubators 400, 410, 420 are inserted here. These incubators may each, for example, be configured to receive a microwell plate or an Erlenmeyer flask as a sample carrier. In addition, even larger incubators may be inserted in principle.

The shelving system 300 is so designed that incubators of various sizes may be used. Both the incubators and the shelving system comply with a predetermined grid size.

Figure 5:
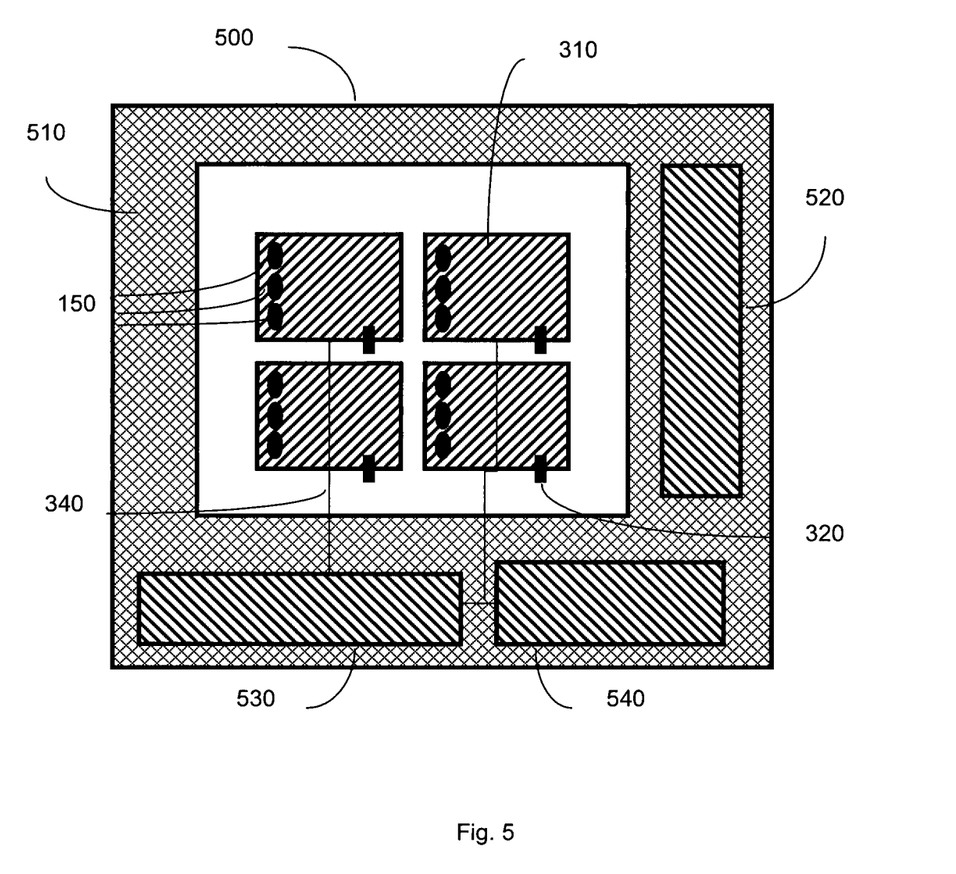
FIG. 5 shows a section through a transport container according to the invention.

If incubated samples need to be transported over long distances or time periods, the incubators 310 may be inserted into a transport container 500, as shown schematically in FIG. 5. This transport container 500 is thermally insulated 510 and may accommodate multiple incubators 310 according to the invention. For this purpose, it has appropriate guiding and locking devices 320. In addition to a battery pack 520 for the power supply, the transport container 500 also has a water tank 530 and a $CO_2$ tank 540 as well as leads 340 to the receiving points for the incubators and the matching connections 150 at these receiving points. Thus, the supply of the incubators may be ensured for typical transport duration.

GLOSSARY

Data Logger

A data logger is a processor-controlled storage unit, which receives the data in a certain rhythm via an interface and stores it on a storage medium. It consists of a programmable microprocessor, a storage medium, at least one interface and one or a plurality of channels for connecting to data sources, such as e.g. sensors. The storage rhythm depends on the specific use. The storage process may be carried out at precise intervals or at the time of the respective data generation. In any event, the storage process is always fully automatic. For specific applications in sensor technology, a data logger may consist of special hardware combined with sensors to detect the physical measurement data such as temperatures, voltages and accelerations over a certain period of time. (According to de.wikipedia.org/wiki/data logger)

Incubator

An incubator is a device in biology, with which controlled external conditions may be created and maintained for different development and growth processes. It is used to create and maintain a microclimate with closely controlled humidity and temperature conditions. The incubator has a timer and a thermostat and possibly an adjustment to regulate the fresh air supplied. The set temperature is adjusted to the optimum temperature for the microorganisms to be incubated. $CO_2$ incubators may be used for the cultivation of animal cells. (According to de.wikipedia.org/wiki/Inkubator_(Biologie))

Microwell Plate/Microplate

A microwell plate is a multiple sample carrier The rectangular microwell plates are usually made of plastic or, for very special applications, glass. They contain between 6 (2×3) and 1536 (32×48) wells isolated from each other in rows and columns. The exact dimensions (Length×Width× Height) are 127.76×85.48×14.35 mm, in accordance with the ANSI standard recommended by the Society for Biomolecular Screening (SBS). Microwell plates are used for a wide variety of microbiological operations. Typical applications include cell culture or screening technical bioreactions. Due to the large number of wells and the use of the same types, microwell plates are suitable for culturing and testing large numbers of samples. Due to the normalized size, almost all operations may be automated with suitable robots. (According to de.wikipedia.org/wiki/Mikrotiterplatte)

Petri Dish

A petri dish is a flat, round, transparent dish with an overlapping cover, which is generally used in biology, medicine or chemistry. (According to de.wikipedia.org/wiki/Petrischale)

Sample Carrier

Microbiological samples or cell cultures are kept in containers that are referred to herein as sample carriers. Depending on the nature of the sample, this may involve various containers. Typically, however, Petri dishes or microwell plates (so-called microplates) are used, sometimes also Erlenmeyer flasks or similar. Multiple sample carriers, for example microwell plates, are also referred to as sample carrier systems.

LIST OF REFERENCE NUMERALS

100 Shelving system (section)
110 Top of the incubator
120 Gas outlet
130 Unlocking switch
140 Underside of the incubator
150 Supply connection
160 Control lamp on the incubator
170 Indicator lights on the shelving system
200 Inner shell
210 Heating element
220 Recess for electronic module
230 Electronic module
240 Battery
250 Sensors
300 Shelving system
310 Incubator, smallest version
320 Guiding and locking device
330 Supply unit
340 Lead
350 System assembly connector
400 Incubator, small version
410 Incubator, medium version
420 Incubator, large version
500 Transport container
510 Thermal insulation
520 Battery pack
530 Water tank
540 $CO_2$ tank

LITERATURE CITED

Patent Literature

U.S. Pat. No. 6,518,059 B1
DE 10 2005 036 763 A1

The invention claimed is:

1. A system comprising a plurality of incubators for the respective reception of an individual sample carrier, wherein each individual incubator comprises:
   supply connections for electricity, at least one gas, and vaporous or liquid water;
   at least one valve actuator configured to control valves to adjust the gas and water flow entering the respective incubator via the respective supply connections, whereby the respective gas content and humidity may be influenced;
   wherein the valves are located at external counterparts to the supply connections of the incubator, and are external to the incubator;
   a transceiver configured to establish a wireless connection with at least one computer or computer network, such that the actual or target values for the gas content and humidity may be queried and the at least one valve actuator controlled to adjust or regulate the flow of gas or water when the wireless connection is established;

an individual control unit that automatically regulates the temperature of an interior of the incubator and the gas and water flow entering said incubator by the respective supply connections; and a lower shell and an upper shell, wherein each of the lower shell and upper shell comprising an inner shell and an outer shell and wherein the inner shell is replaceable; wherein each incubator further comprises a storage device for electrical energy capable of supplying energy without an external power supply.

2. The system of claim 1, each of the plurality of incubators further comprising:

sensors configured to determine a temperature, humidity and content of the at least one gas in the interior of the respective incubator.

3. The system of claim 1, each further comprising a gas outlet.

4. The system of claim 1, each further comprising a filter system for the individual supply connections or the gas outlet, wherein the filter system is configured such that contamination of the interior of the incubator is excluded, and contamination of the supply connections or the ambient air is excluded.

5. The system of claim 1, wherein each of the incubators has a unique identification address, which is an individual IP address.

6. The system of claim 2, each further comprising a data logger that caches the values currently determined by the respective sensors when there is no connection with at least one computer or computer network.

7. The system of claim 1, wherein the lower shell and upper shell are made of thermally insulating material.

8. The system of claim 1, wherein each individual incubator further comprises a port configured to establish communication via USB or Ethernet connection with at least one computer or computer network.

9. The system of claim 1, each further comprising a semi-permeable membrane on the respective sample carrier.

10. The modular incubator system of claim 1, wherein each individual incubator further comprises a replaceable inner shell.

11. The modular incubator system of claim 1, wherein the storage device for electrical energy comprises a battery pack.

12. A shelving system comprising: a plurality of incubators for the respective reception of an individual sample carrier, wherein each individual incubator comprises:

supply connections for electricity, at least one gas, and vaporous or liquid water;

at least one valve actuator configured to control valves to adjust the gas and water flow entering the respective incubator via the respective supply connections, whereby the respective gas content and humidity may by influenced;

wherein the valves are located at external counterparts to the supply connections of the incubator, and are external to the incubator;

a transceiver configured to establish a wireless connection with at least one computer or computer network, such that the actual or target values for the gas content and humidity may be queried and the at least one valve actuator controlled to adjust or regulate the flow of gas or water when the wireless connection is established;

an individual control unit that automatically regulates the temperature of an interior of the incubator and the gas and water flow entering said incubator by the respective supply connections; and a lower shell and an upper shell, wherein each of the lower shell and upper shell comprising an inner shell and an outer shell and wherein the inner shell is replaceable; wherein each incubator further comprises a storage device for electrical energy capable of supplying energy without an external power supply; wherein the dimensions of the incubators comply with a grid and have identical or different sizes, and wherein the shelving system is adapted to the grid of the incubators and allows withdrawal and insertion of those incubators arranged below other incubators without affecting the incubators arranged above, and wherein the shelving system has individual supply connections for electricity, at least one gas, and vaporous or liquid water for each of the plurality of incubators.

13. The shelving system of claim 12, further comprising a data interface for each of the plurality of incubators.

14. The shelving system of claim 12, further comprising:

a locking mechanism configured to:

fixedly connect individual incubators to the shelving system, and release the individual incubators independently of one another.

15. A modular incubator system, comprising:

a shelving system to receive the plurality of incubators of claim 1, wherein the dimensions of the incubators comply with a grid and have identical or different sizes, and wherein the shelving system is adapted to the grid of the incubators and allows withdrawal and insertion of those incubators arranged below other incubators without affecting the incubators arranged above, and wherein the shelving system has individual supply connections for electricity, at least one gas, and vaporous or liquid water for each of the plurality of incubators;

the plurality of incubators according to claim 1; and at least one transport container to receive at least one incubator according to claim 1, wherein the transport container comprises:

a storage device for electrical energy;

reservoirs for water and at least one gas;

supply connections to provide electricity to the at least one incubator; and supply connections to provide (i) at least one gas and (ii) vaporous or liquid water to the at least one incubator.

16. The modular incubator system of claim 15, wherein a part of the transport container configured to receive the at least one incubator comprises thermal insulation.

17. The modular incubator system of claim 15, wherein each of the plurality of incubators further comprises: sensors configured to determine a temperature, humidity and content of the at least one gas in the interior of the respective incubator, where the transport container is configured from the plurality of incubators according to claim 2; and wherein the transport container further comprises memory for storing currently determined values from the sensors of the at least one incubator when the at least one incubator is located in the transport container.

* * * * *

UNITED STATES PATENT AND TRADEMARK OFFICE
CERTIFICATE OF CORRECTION

PATENT NO. : 11,220,664 B2
APPLICATION NO. : 15/311273
DATED : January 11, 2022
INVENTOR(S) : Robin Christopher Zander, Erwin Thiel and Stephan Irle Page 1 of 1

It is certified that error appears in the above-identified patent and that said Letters Patent is hereby corrected as shown below:

In the Claims

At Column 9, Lines 53 and 54, change "humidity may by influenced;" to --humidity may be influenced;--

At Column 10, Lines 58 and 59, change "wherein the transport container is configured from the plurality of incubators according to claim 2; and" to --wherein the transport container is configured to receive at least one incubator from the plurality of incubators; and--

Signed and Sealed this
First Day of November, 2022

Katherine Kelly Vidal
*Director of the United States Patent and Trademark Office*